(12) United States Patent
Fanger et al.

(10) Patent No.: US 9,161,782 B2
(45) Date of Patent: *Oct. 20, 2015

(54) BONE ANCHOR ASSEMBLIES AND METHODS OF MANUFACTURING AND USE THEREOF

(71) Applicant: DePuy Synthes Products, LLC, Raynham, MA (US)

(72) Inventors: Jonathan Fanger, Raynham, MA (US); Andrew P Dooris, Raynham, MA (US); Leigh W Potter, Plymouth, MA (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 79 days.

This patent is subject to a terminal disclaimer.

(21) Appl. No.: 13/740,403

(22) Filed: Jan. 14, 2013

(65) Prior Publication Data
US 2013/0131731 A1 May 23, 2013

Related U.S. Application Data

(63) Continuation of application No. 12/580,777, filed on Oct. 16, 2009, now Pat. No. 8,361,123.

(51) Int. Cl.
*A61B 17/70* (2006.01)
*A61B 17/86* (2006.01)

(52) U.S. Cl.
CPC ......... *A61B 17/7034* (2013.01); *A61B 17/7037* (2013.01); *A61B 17/7032* (2013.01); *A61B 17/864* (2013.01); *Y10T 29/49826* (2015.01)

(58) Field of Classification Search
CPC ........... A61B 17/7032; A61B 17/7034; A61B 17/7037
USPC ......................................... 606/246, 254–279
See application file for complete search history.

(56) References Cited

U.S. PATENT DOCUMENTS

| 5,034,011 A | 7/1991 | Howland |
| 5,098,434 A | 3/1992 | Serbousek |
| 5,102,412 A | 4/1992 | Rogozinski |
| 5,108,399 A | 4/1992 | Eitenmuller |

(Continued)

FOREIGN PATENT DOCUMENTS

| CN | 201085681 | 7/2008 |
| EP | 289192 | 1/1992 |

(Continued)

OTHER PUBLICATIONS

Baldwin, "Sacral Fixation Using Iliac Instrumentation and a Variable-Angle Screw Device"; J. Neurosurg; 1994; pp. 313-316; vol. 81.

(Continued)

*Primary Examiner* — Anu Ramana

(57) ABSTRACT

A bone anchor assembly includes a bone anchor having a proximal head and a distal shaft configured to engage bone, a receiver member for receiving a spinal fixation element to be coupled to the bone anchor, an insert positioned in the proximal end of the receiver member having a pair of spaced apart insert arms defining a recess therebetween, and a closure mechanism positionable between and engaging the insert arms to capture a spinal fixation element within the recess of the insert and fix the spinal fixation element with respect to the receiver member.

20 Claims, 6 Drawing Sheets

(56) References Cited

U.S. PATENT DOCUMENTS

| | | |
|---|---|---|
| 5,147,360 A | 9/1992 | Dubousset |
| 5,180,393 A | 1/1993 | Commarmond |
| 5,181,917 A | 1/1993 | Rogozinski |
| 5,217,497 A | 6/1993 | Mehdian |
| 5,261,907 A | 11/1993 | Vignaud |
| 5,360,448 A | 11/1994 | Thramann |
| 5,368,594 A | 11/1994 | Martin |
| 5,375,823 A | 12/1994 | Navas |
| 5,443,467 A | 8/1995 | Biedermann |
| 5,480,438 A | 1/1996 | Arima |
| 5,498,263 A | 3/1996 | DiNello |
| 5,501,684 A | 3/1996 | Schlapfer |
| 5,505,736 A | 4/1996 | Reimels |
| 5,520,689 A | 5/1996 | Schlapfer |
| 5,549,677 A | 8/1996 | Durr |
| 5,562,663 A | 10/1996 | Wisnewski |
| 5,571,102 A | 11/1996 | Cavagna |
| 5,584,831 A | 12/1996 | McKay |
| 5,586,984 A | 12/1996 | Errico |
| 5,591,166 A | 1/1997 | Bernhardt |
| 5,630,817 A | 5/1997 | Rokegem |
| 5,643,260 A | 7/1997 | Doherty |
| 5,647,873 A | 7/1997 | Errico |
| 5,669,911 A | 9/1997 | Errico |
| 5,672,176 A | 9/1997 | Biedermann |
| 5,683,390 A | 11/1997 | Metz Stavenhagen |
| 5,688,274 A | 11/1997 | Errico |
| 5,690,630 A | 11/1997 | Errico |
| 5,725,528 A | 3/1998 | Errico |
| 5,728,098 A | 3/1998 | Sherman |
| 5,733,285 A | 3/1998 | Errico |
| 5,735,851 A | 4/1998 | Errico |
| 5,738,685 A | 4/1998 | Halm |
| 5,782,833 A | 7/1998 | Haider |
| 5,790,543 A | 8/1998 | Cloutier |
| 5,797,911 A | 8/1998 | Sherman |
| 5,810,819 A | 9/1998 | Errico |
| 5,817,094 A | 10/1998 | Errico |
| 5,863,293 A | 1/1999 | Richelsoph |
| 5,879,350 A | 3/1999 | Sherman |
| 5,882,350 A | 3/1999 | Ralph |
| 5,885,286 A | 3/1999 | Sherman |
| 5,891,145 A | 4/1999 | Morrison |
| 5,902,303 A | 5/1999 | Eckhof |
| 5,910,142 A | 6/1999 | Tatar |
| 5,954,725 A | 9/1999 | Sherman |
| 5,961,516 A | 10/1999 | Graf |
| 5,964,760 A | 10/1999 | Richelsoph |
| 5,997,539 A | 12/1999 | Errico |
| 6,004,349 A | 12/1999 | Jackson |
| 6,007,539 A | 12/1999 | Kirsch |
| 6,010,503 A | 1/2000 | Richelsoph |
| 6,022,350 A | 2/2000 | Ganem |
| 6,050,997 A | 4/2000 | Mullane |
| 6,053,917 A | 4/2000 | Sherman |
| 6,063,090 A | 5/2000 | Schlapfer |
| 6,077,262 A | 6/2000 | Schlapfer |
| 6,083,226 A | 7/2000 | Fiz |
| 6,090,110 A | 7/2000 | Metz Stavenhagen |
| 6,113,601 A | 9/2000 | Tatar |
| 6,132,432 A | 10/2000 | Richelsoph |
| 6,132,434 A | 10/2000 | Sherman |
| 6,139,549 A | 10/2000 | Keller |
| 6,146,383 A | 11/2000 | Studer |
| 6,183,472 B1 | 2/2001 | Lutz |
| 6,214,006 B1 | 4/2001 | Metz Stavenhagen |
| 6,224,598 B1 | 5/2001 | Jackson |
| 6,248,105 B1 | 6/2001 | Schläpfer |
| 6,251,112 B1 | 6/2001 | Jackson |
| 6,254,602 B1 | 7/2001 | Jtis |
| 6,261,287 B1 | 7/2001 | Metz Stavenhagen |
| 6,280,442 B1 | 8/2001 | Barker |
| 6,287,311 B1 | 9/2001 | Sherman |
| 6,302,888 B1 | 10/2001 | Mellinger |
| 6,355,040 B1 | 3/2002 | Richelsoph |
| 6,361,535 B2 | 3/2002 | Jackson |
| RE37,665 E | 4/2002 | Ralph |
| 6,371,957 B1 | 4/2002 | Amrein |
| 6,379,356 B1 | 4/2002 | Jackson |
| 6,402,752 B2 | 6/2002 | Schäffler-Wachter |
| 6,440,132 B1 | 8/2002 | Jackson |
| 6,454,773 B1 | 9/2002 | Sherman |
| 6,471,705 B1 | 10/2002 | Biedermann |
| 6,471,707 B1 | 10/2002 | Miller |
| 6,482,207 B1 | 11/2002 | Errico |
| 6,485,494 B1 | 11/2002 | Haider |
| 6,488,681 B2 | 12/2002 | Martin |
| 6,520,963 B1 | 2/2003 | McKinley |
| 6,521,264 B1 | 2/2003 | Lacout |
| 6,537,276 B2 | 3/2003 | Metz Stavenhagen |
| 6,540,749 B2 | 4/2003 | Schäfer |
| 6,547,792 B1 | 4/2003 | Tsuji |
| 6,554,834 B1 | 4/2003 | Crozet |
| 6,565,567 B1 | 5/2003 | Haider |
| 6,565,569 B1 | 5/2003 | Assaker |
| 6,569,164 B1 | 5/2003 | Assaker |
| 6,582,436 B2 | 6/2003 | Schlapfer |
| 6,626,908 B2 | 9/2003 | Cooper |
| 6,641,583 B2 | 11/2003 | Shluzas |
| 6,652,526 B1 | 11/2003 | Arafiles |
| 6,660,004 B2 | 12/2003 | Barker |
| 6,663,634 B2 | 12/2003 | Ahrens |
| 6,672,788 B2 | 1/2004 | Hathaway |
| 6,716,214 B1 | 4/2004 | Jackson |
| 6,726,687 B2 | 4/2004 | Jackson |
| 6,730,089 B2 | 5/2004 | Jackson |
| 6,733,503 B2 | 5/2004 | Layrolle |
| 6,749,612 B1 | 6/2004 | Conchy |
| 6,755,829 B1 | 6/2004 | Bono |
| 6,786,903 B2 | 9/2004 | Lin |
| 6,835,196 B2 | 12/2004 | Biedermann |
| 6,869,433 B2 | 3/2005 | Glascott |
| 6,881,215 B2 | 4/2005 | Assaker |
| 6,887,242 B2 | 5/2005 | Doubler |
| 6,896,677 B1 | 5/2005 | Lin |
| 6,905,500 B2 | 6/2005 | Jeon |
| 6,916,321 B2 | 7/2005 | TenHuisen |
| 6,918,911 B2 | 7/2005 | Biedermann |
| 7,008,423 B2 | 3/2006 | Assaker |
| 7,022,122 B2 | 4/2006 | Amrein |
| RE39,089 E | 5/2006 | Ralph |
| 7,063,702 B2 | 6/2006 | Michelson |
| 7,090,674 B2 | 8/2006 | Doubler |
| 7,156,850 B2 | 1/2007 | Kim |
| 7,179,261 B2 | 2/2007 | Sicvol |
| 7,186,255 B2 | 3/2007 | Baynham |
| 7,204,838 B2 | 4/2007 | Jackson |
| 7,211,086 B2 | 5/2007 | Biedermann |
| 7,261,714 B2 | 8/2007 | Richelsoph |
| 7,306,606 B2 | 12/2007 | Sasing |
| 7,322,981 B2 | 1/2008 | Jackson |
| 7,326,210 B2 | 2/2008 | Jahng |
| 7,476,228 B2 | 1/2009 | Abdou |
| 7,604,655 B2 | 10/2009 | Warnick |
| 7,622,172 B2 | 11/2009 | Keenan |
| 7,625,394 B2 * | 12/2009 | Molz et al. .......... 606/270 |
| 7,625,396 B2 | 12/2009 | Jackson |
| 7,662,172 B2 | 2/2010 | Warnick |
| 7,862,588 B2 * | 1/2011 | Abdou .......... 606/246 |
| 8,012,185 B2 | 9/2011 | Warnick |
| 8,361,123 B2 | 1/2013 | Fanger |
| 2002/0151900 A1 | 10/2002 | Glascott |
| 2002/0183748 A1 | 12/2002 | Martin |
| 2003/0004512 A1 | 1/2003 | Farris |
| 2003/0032957 A1 | 2/2003 | McKinley |
| 2003/0109880 A1 | 6/2003 | Shirado |
| 2003/0120280 A1 | 6/2003 | Roller |
| 2003/0125741 A1 | 7/2003 | Biedermann |
| 2003/0149432 A1 | 8/2003 | Frigg |
| 2004/0049189 A1 | 3/2004 | Le Couedic |
| 2004/0049190 A1 | 3/2004 | Biedermann |
| 2004/0097933 A1 | 5/2004 | Lourdel |
| 2004/0102781 A1 | 5/2004 | Jeon |
| 2004/0106925 A1 | 6/2004 | Culbert |

(56) References Cited

U.S. PATENT DOCUMENTS

| | | |
|---|---|---|
| 2004/0111088 A1 | 6/2004 | Picetti |
| 2004/0127899 A1 | 7/2004 | Konieczynski |
| 2004/0143264 A1 | 7/2004 | McAfee |
| 2004/0143267 A1 | 7/2004 | Fallin |
| 2004/0158247 A1 | 8/2004 | Sitiso |
| 2004/0172022 A1 | 9/2004 | Landry |
| 2004/0181224 A1 | 9/2004 | Biedermann |
| 2004/0225289 A1 | 11/2004 | Biedermann |
| 2004/0236327 A1 | 11/2004 | Paul |
| 2004/0236328 A1 | 11/2004 | Paul |
| 2004/0236330 A1 | 11/2004 | Purcell |
| 2004/0267264 A1 | 12/2004 | Konieczynski |
| 2005/0027292 A1 | 2/2005 | Bernard |
| 2005/0038438 A1 | 2/2005 | Anderson |
| 2005/0049588 A1 | 3/2005 | Jackson |
| 2005/0049589 A1 | 3/2005 | Jackson |
| 2005/0055026 A1 | 3/2005 | Biedermann |
| 2005/0065514 A1 | 3/2005 | Studer |
| 2005/0096654 A1 | 5/2005 | Lin |
| 2005/0165396 A1 | 7/2005 | Fortin |
| 2005/0171542 A1 | 8/2005 | Biedermann |
| 2005/0171543 A1 | 8/2005 | Timm |
| 2005/0177156 A1 | 8/2005 | Timm |
| 2005/0182401 A1 | 8/2005 | Timm |
| 2005/0187549 A1 | 8/2005 | Jackson |
| 2005/0203516 A1 | 9/2005 | Biedermann |
| 2005/0222569 A1 | 10/2005 | Panjabi |
| 2005/0245930 A1 | 11/2005 | Timm |
| 2005/0261685 A1 | 11/2005 | Fortin |
| 2005/0273101 A1 | 12/2005 | Schumacher |
| 2005/0277920 A1 | 12/2005 | Slivka |
| 2005/0277922 A1 | 12/2005 | Trieu |
| 2005/0277928 A1 | 12/2005 | Boschert |
| 2005/0288670 A1 | 12/2005 | Panjabi |
| 2006/0025767 A1 | 2/2006 | Khalili |
| 2006/0036252 A1 | 2/2006 | Baynham |
| 2006/0041259 A1 | 2/2006 | Paul |
| 2006/0084981 A1 | 4/2006 | Shluzas |
| 2006/0100621 A1 | 5/2006 | Jackson |
| 2006/0100622 A1 | 5/2006 | Jackson |
| 2006/0142772 A1 | 6/2006 | Ralph |
| 2006/0149231 A1 | 7/2006 | Bray |
| 2006/0149232 A1 | 7/2006 | Sasing |
| 2006/0149235 A1 | 7/2006 | Jackson |
| 2006/0149240 A1 | 7/2006 | Jackson |
| 2006/0149244 A1 | 7/2006 | Amrein |
| 2006/0161152 A1 | 7/2006 | Ensign |
| 2006/0190002 A1 | 8/2006 | Tallarida |
| 2006/0247631 A1 | 11/2006 | Ahn |
| 2006/0264937 A1 | 11/2006 | White |
| 2006/0276788 A1 | 12/2006 | Berry |
| 2006/0293659 A1 | 12/2006 | Alvarez |
| 2007/0049933 A1 | 3/2007 | Ahn |
| 2007/0055240 A1 | 3/2007 | Matthis |
| 2007/0055241 A1 | 3/2007 | Matthis |
| 2007/0118117 A1 | 5/2007 | Altarac |
| 2007/0161985 A1 | 7/2007 | Demakas |
| 2007/0191835 A1 | 8/2007 | Jtis |
| 2007/0233078 A1 | 10/2007 | Jtis |
| 2007/0270838 A1 | 11/2007 | Bruneau |
| 2008/0004625 A1 | 1/2008 | Runco |
| 2008/0015576 A1 | 1/2008 | Whipple |
| 2008/0015579 A1 | 1/2008 | Whipple |
| 2008/0015580 A1 | 1/2008 | Chao |
| 2008/0015596 A1 | 1/2008 | Whipple |
| 2008/0015597 A1 | 1/2008 | Whipple |
| 2008/0033435 A1 | 2/2008 | Studer |
| 2008/0125816 A1 | 5/2008 | Jackson |
| 2008/0132957 A1 | 6/2008 | Matthis |
| 2008/0177323 A1 | 7/2008 | Null |
| 2008/0234761 A1 | 9/2008 | Jackson |
| 2008/0269809 A1 | 10/2008 | Garamszegi |
| 2008/0287998 A1 | 11/2008 | Doubler |
| 2008/0288003 A1 | 11/2008 | McKinley |
| 2008/0306554 A1 | 12/2008 | McKinley |
| 2009/0024174 A1 | 1/2009 | Stark |
| 2009/0036893 A1 | 2/2009 | Kartalian |
| 2009/0036934 A1 | 2/2009 | Biedermann |
| 2009/0087472 A1 | 4/2009 | Murphy |
| 2010/0057125 A1* | 3/2010 | Viker .................. 606/246 |

FOREIGN PATENT DOCUMENTS

| | | |
|---|---|---|
| EP | 599766 | 6/1994 |
| EP | 532421 | 11/1995 |
| EP | 465158 | 1/1997 |
| EP | 767636 | 1/1999 |
| EP | 1776927 | 5/2007 |
| EP | 1747760 | 10/2009 |
| WO | 9322983 | 11/1993 |
| WO | 9407425 | 4/1994 |
| WO | 9501132 | 1/1995 |
| WO | 9513755 | 5/1995 |
| WO | 9531158 | 11/1995 |
| WO | 9702786 | 1/1997 |
| WO | 9902200 | 1/1999 |
| WO | 9938451 | 8/1999 |
| WO | 02069854 | 9/2002 |
| WO | 03041599 | 5/2003 |
| WO | 2004064653 | 8/2004 |
| WO | 2005027761 | 3/2005 |
| WO | 2006089292 | 8/2006 |
| WO | 2006115539 | 11/2006 |
| WO | 2006116437 | 11/2006 |
| WO | 2007067857 | 6/2007 |
| WO | 2007075454 | 7/2007 |
| WO | 2008003047 | 6/2008 |

OTHER PUBLICATIONS

Fogel, "Physical Characteristics of Polyaxial-Headed Pedicle Screws and Biochemical Comparison of Load With Their Failure"; Spine; Mar. 1, 2003; pp. 397-401; vol. 28(5); Lippincott Williams & Wilkins.

Harms, "Posterior C1-C2 Fusion With Polyaxial Screw and Rod Fixation"; Spine; Nov. 15, 2001; pp. 2467-71; vol. 26(22); Lippincott Williams & Wilkins.

McGee, "A Simplified Galveston Technique for the Stabilization of Pathological Fractures of the Sacrum"; Eur. Spine J.; 2009; pp. 451-454; vol. 9.

Mumaneni, "Posterior Cervical Fixation Using a New Polyaxial Screw and System: Technique and Surgical Results"; Neurosurg Focus; Jan. 15, 2002; pp. 1-5; vol. 12(1); Article 8.

Schultheiss, "MACS TL Polyaxialscrew XL A New Concept to Increase the Stability of Ventral Spondylodesis in the Presence of Dorsal Structure Injuries"; Orthopade; Apr. 2002; pp. 397-401; vol. 31(4); Springer-Verlag.

Stokes, "Posterior Atlantoaxial Stabilization New Alternative to C1-C2 Transarticular Screw"; Neurosurg Focus; Jan. 15, 2002; pp. 1-5; vol. 12(1); Article 6.

Stulik, "Combined Atlantoaxial Fractures"; Acta Chir Orthop Traumatol Cech; 2005; pp. 105-110; vol. 72(2).

* cited by examiner

FIG. 2
FIG. 3
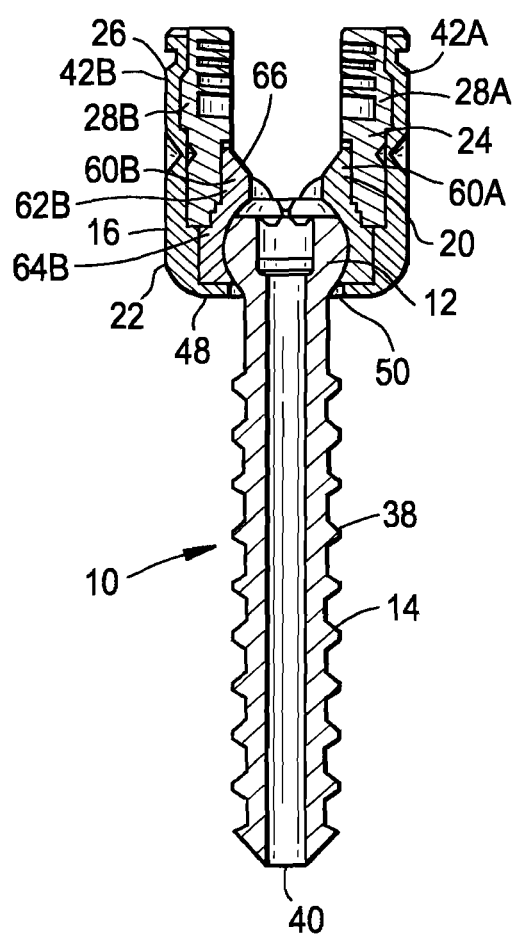
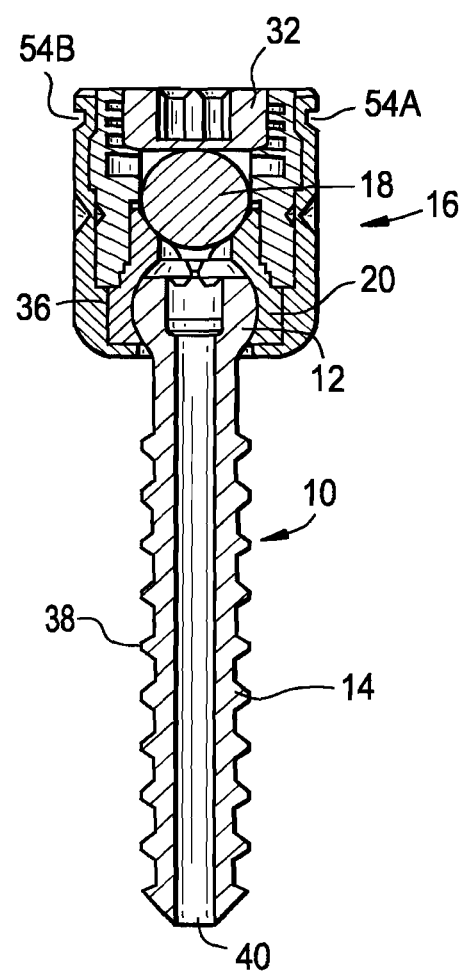

BONE ANCHOR ASSEMBLIES AND METHODS OF MANUFACTURING AND USE THEREOF

CONTINUING DATA

This patent application is a continuation of U.S. Ser. No. 12/580,777, filed Oct. 16, 2009, which is incorporated by reference in its entirety.

BACKGROUND

Bone anchors may be used in orthopedic surgery to fix bone during the healing or fusion process. In spinal surgery, bone anchors may be used with spinal fixation elements, such as spinal rods, to stabilize multiple vertebrae either rigidly, in which no relative motion between the vertebrae is desired, and dynamically, in which limited, controlled motion between the vertebrae is desired.

SUMMARY

Disclosed herein are improved bone anchor assemblies and methods of manufacturing and using bone anchoring assemblies, in particular, bone anchor assemblies used in connection with spinal fixation elements to fix multiple vertebrae either rigidly or dynamically.

According to one aspect, a bone anchor assembly may comprise a bone anchor having a proximal head and a distal shaft configured to engage bone, a receiver member for receiving a spinal fixation element to be coupled to the bone anchor, a bearing positioned in the distal end of the receiver member and receiving the proximal head of the bone anchor, an insert positioned in the proximal end of the receiver member having a pair of spaced apart insert arms defining a recess therebetween, and a closure mechanism positionable between and engaging the insert arms to capture a spinal fixation element within the recess of the insert and fix the spinal fixation element with respect to the receiver member. The receiver member may have a proximal end having a pair of spaced apart arms defining a recess therebetween and a distal end having a distal end surface defining opening through which at least a portion of the bone anchor extends. At least a portion of the bearing may be interposed between the proximal head of the bone anchor and the distal end surface of the distal end of the receiver member. The insert recess may be sized and shaped to receive the spinal fixation element and each insert arm may be aligned with and positioned against an interior surface of a respective arm of the receiver member.

According to another aspect, a method of assembling a bone anchor assembly may comprise inserting a distal shank of a bone anchor through a distal opening in a distal end of a receiver member, the receiver member having a proximal end having a pair of spaced apart arms defining a recess therebetween, inserting a bearing and a proximal head of the bone anchor within the distal end of the receiver member, positioning the bearing about the proximal head of a bone anchor, positioning the bearing against a distal end surface of the distal end of the receiver member, at least a portion of the bearing being interposed between the proximal head and the distal end surface of the distal end of the receiver member, positioning an insert having a pair of opposed arms forming a U-shaped recess within the receiver member, the U-shaped recess being sized and shaped to receive a spinal fixation element, aligning each insert arm with an interior surface of a respective arm of the receiver member and the U-shaped recess of the insert with the recess in the proximal end of the receiver member, and securing the insert to the receiver member.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

FIG. 2 is a side view in cross section of the bone anchor assembly of FIG. 1, FIG. 3 is a side view in cross section of the bone anchor assembly of FIG. 1, illustrating a spinal rod secured to the bone anchor assembly by a closure mechanism.

DETAIL DESCRIPTION OF EXEMPLARY EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Figure 1:
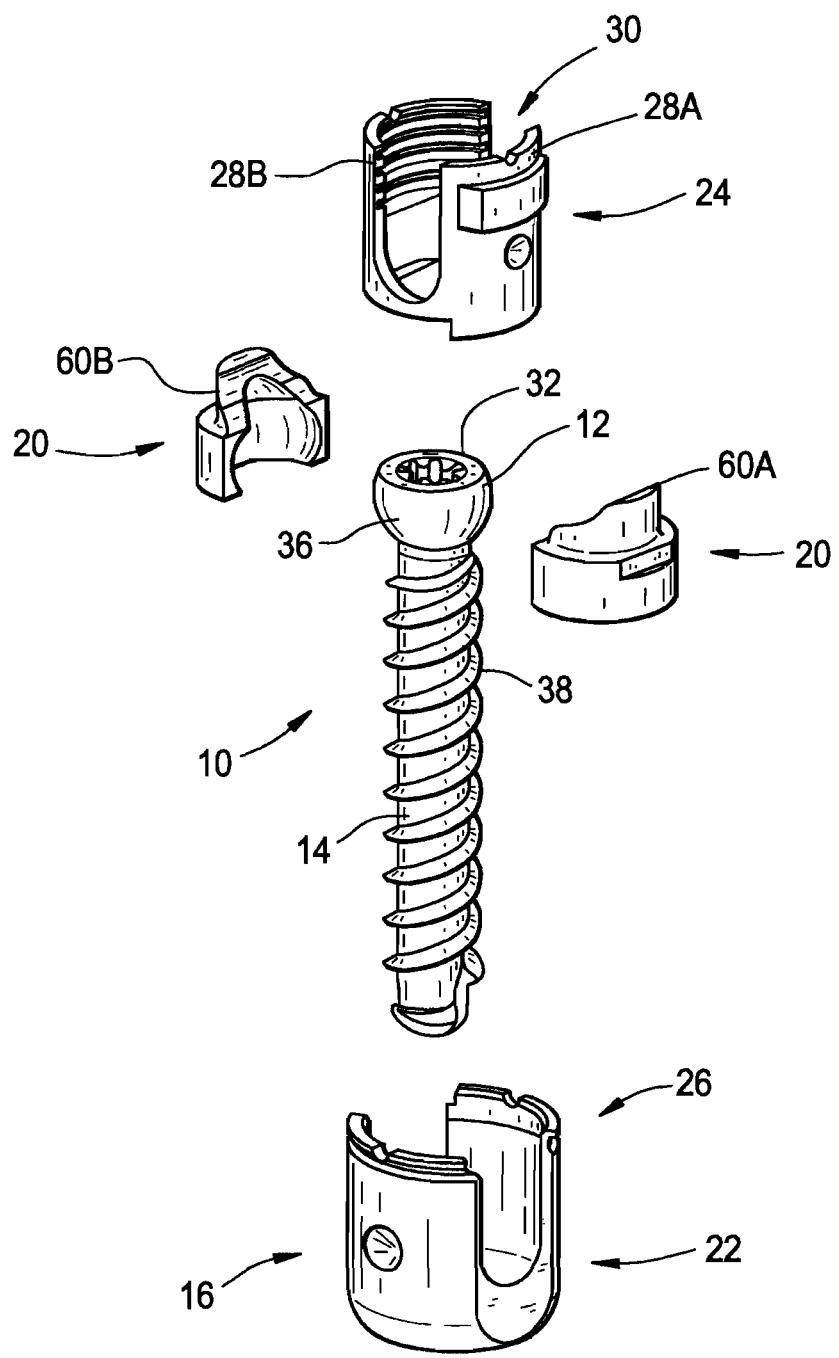
FIG. 1 is an exploded view of an exemplary embodiment of a bone anchor assembly.

FIGS. 1-3 illustrate an exemplary embodiment of a bone anchor assembly including a bone anchor 10 having a proximal head 12 and a distal shaft 14 configured to engage bone, a receiver member 16 for receiving a spinal fixation element 18 to be coupled to the bone anchor 10, a bearing 20 positioned in the distal end 22 of the receiver member 16 and receiving the proximal head 12 of the bone anchor 10, an insert 24 positioned in the proximal end 26 of the receiver member 16 having a pair of spaced apart insert arms 28A, 28B defining a recess 30 therebetween, and a closure mechanism 32 positionable between and engaging the insert arms 28A, 28B to capture the spinal fixation element 18 within the recess 30 of the insert 24 and fix the spinal fixation element 18 with respect to the receiver member 16.

The proximal head 12 of the bone anchor 10 in the exemplary embodiment is generally in the shape of a truncated sphere having a planar proximal surface 32 and an approximately spherically shaped distal surface 36. The exemplary bone anchor assembly is a polyaxial bone screw. In this regards, the proximal head 12 of the bone anchor 10 engages the bearing 20 in a ball and socket like arrangement in which the proximal head 12, and thus the distal shaft 14, can pivot relative to the bearing 20 and the receiver member 16. The distal surface 36 of the bone anchor 10 and the mating surface of the bearing 20 may have any shape that facilitates this ball and socket like arrangement, including, for example, spherical (as illustrated), toroidal, conical, frustoconical, polyhedral, and any combinations of these shapes.

The distal shaft 14 of the bone anchor 10 may include bone engaging features such as one or more bone engaging threads 38. Any type or shape thread suitable for engaging bone may be employed. In the exemplary embodiment, a dual lead thread is employed. In addition, the bone anchor 10 may be cannulated, having a central lumen or cannula 40 extending the length of the bone anchor 10 to facilitate delivery of the bone anchor 10 over a guide wire in, for example, minimally invasive procedures. The distal shaft 14 may also include one or more openings or fenestrations (not shown) that communicate with the cannula 40 to permit bone in-growth or to permit the dispensing of bone cement or other materials through the bone anchor 10. The distal shaft 14 of the bone anchor 10 may also be coated with materials to permit bone growth, such as, for example, hydroxyl apatite, and the bone anchor 10 may be coated all or in-part with anti-infective materials, such as, for example, tryclosan.

Figure 4:
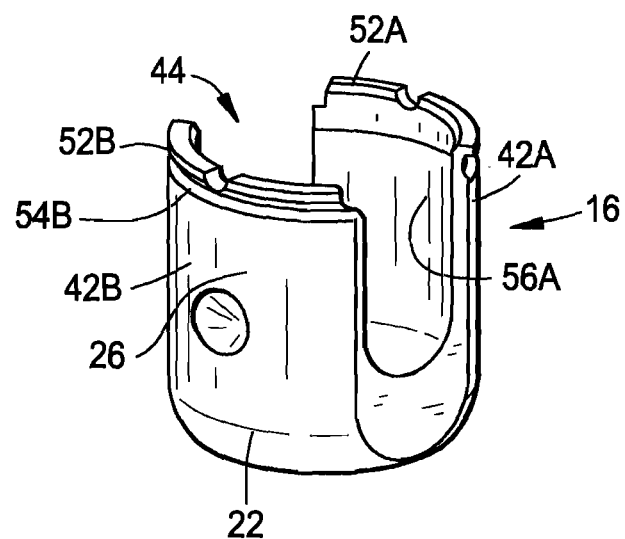
FIG. 4 is a perspective view of the receiver member of the bone anchor assembly of FIG. 1.
Figure 5:
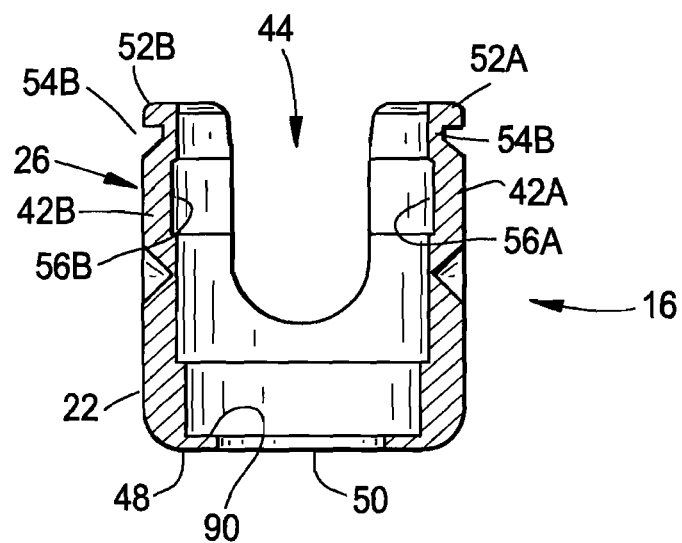
FIG. 5 is a side view in cross section of the receiver member of FIG. 4.

Continuing to refer to FIGS. 1-3 and also referring to FIGS. 4 and 5, the proximal end 26 of the receiver member 16 of the exemplary bone anchor assembly includes a pair of spaced apart arms 42A, 42B defining a U-shaped recess 44 therebetween for receiving both the insert 24 and the spinal fixation element 18. The receiver member 16 includes a distal end 22 that is generally annular in shape and includes a distal end surface 48 defining opening 50 through which at least a portion of the bone anchor 10 extends. For example, the distal shaft 14 of the bone anchor 10 may extend through the opening 50. Each arm 42A, 42B of the proximal end 26 of the receiver member 16 extends from the distal end 22 of the receiver member 16 to a free end 52A, 52B. The outer surface of each arm 42A, 42B may include a feature, such as a recess, dimple, notch, projection, or the like, to facilitate connection of the receiver member 16 and, thus, the bone anchor assembly, to instruments. In the exemplary embodiment, for example, the outer surface of each arm 42A, 42B includes an arcuate groove 54A, 54B at the respective free end 52A, 52B of the arms. Such grooves are described in more detail in U.S. Pat. No. 7,179,261, which is incorporated herein by reference.

The interior surface of each arm 42A, 42B includes a feature, such as a recess, dimple, notch, projection, or the like, to facilitate connection of the insert 24 to the receiver member 16. In the exemplary embodiment, for example, the interior surface of each arm 42A, 42B includes a groove 56A, 56B for receiving a ridge 78A, 78B provided on the outer surface of each arm 28A, 28B of the insert 24.

Figure 6:
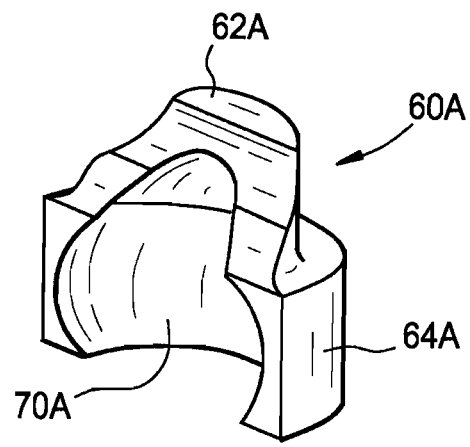
FIG. 6 is a perspective view of one component of the bearing of the bone anchor assembly of FIG. 1.
Figure 7:
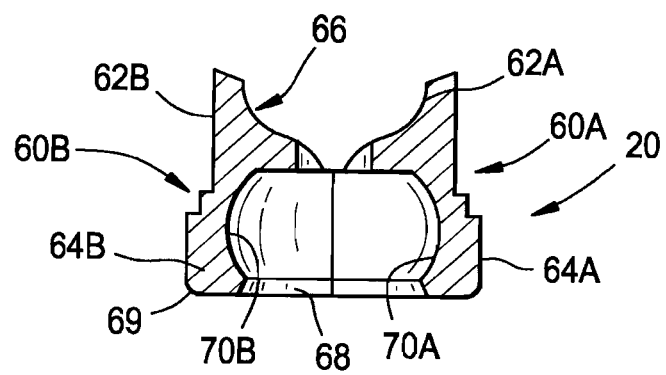
FIG. 7 is a is a side view in cross section of the bearing components of the bone anchor assembly of FIG. 1.
Figure 8:
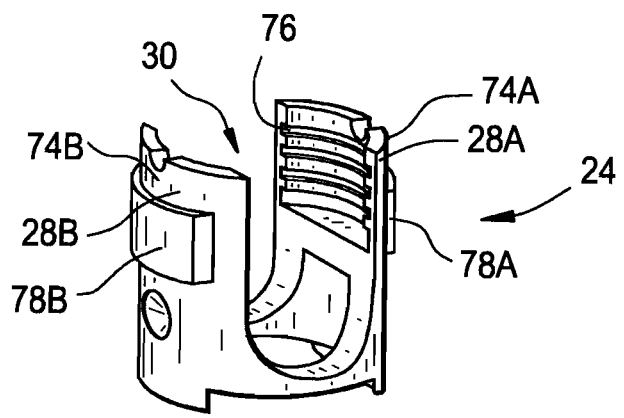
FIG. 8 is a perspective view of the insert of the bone anchor assembly of FIG. 1.
Figure 9:
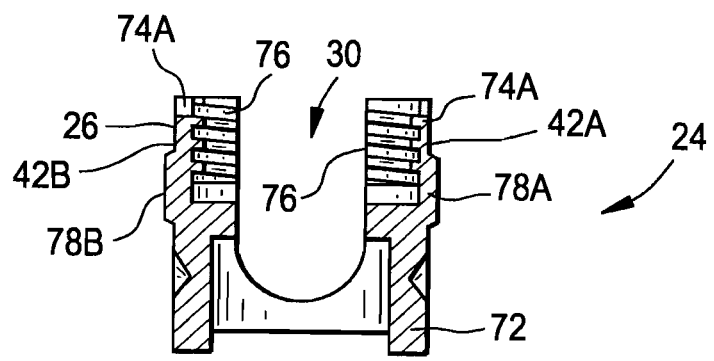
FIG. 9 is a side view in cross section of the insert of FIG. 8.

The exemplary bone anchor assembly is a dynamic or mobile bone anchor assembly in which the bone anchor 10 is adjustable relative receiver member 16 after the spinal fixation element 18 is fixed relative to the receiver member 16. To facilitate the adjustability of the bone anchor 10, the bone anchor assembly includes a bearing 20 positioned within the distal end 22 of the receiver member 16 and positioned about the proximal head 12 of the bone anchor 10. Continuing to refer to FIGS. 1-3 and also referring to FIGS. 6 and 7, the bearing 20 may be a single, unitary construct or may be a multi-piece construct, for example, a two piece construct including a first bearing component 60A and a second bearing component 60B, to facilitate assembly of the bone anchor assembly. The first bearing component 60A and the second bearing component 60B cooperate to surround the proximal head 12 of the bone anchor 10 about the circumference of the proximal head 12. Each bearing component 60A, 60B includes a proximal end 62A, 62B and a distal end 64A, 64B. The proximal ends 62A, 62B of the bearing 20 cooperate to define a U-shaped seat 66 against which the spinal fixation element may be seated when the spinal fixation element 18 is fixed to the receiver member 16. Each distal end 64A, 64B of the bearing 20 is generally arcuate in shape and the distal ends 64A, 64B cooperate to define an annulus having a distal opening 68 in the distal end surface 69 of the bearing 20. When the bearing 20 is positioned within the receiver member 16 about the proximal head 12 of the bone anchor 10, the distal opening 68 of the bearing 20 is aligned with the distal opening 50 of the receiver member 16 and at least a portion of the bone anchor 10, for example, the distal shaft 14, extends through the distal opening 68 of the bearing 20 and the distal opening 50 of the receiver member 16.

Each distal end 64A, 64B of the bearing 20 has an approximately spherical shaped internal surface 70A, 70B for engaging the proximal head 12 of the bone anchor 10. The internal surfaces 70A, 70B may have a curvature that approximates the curvature of the proximal head 12 of the bone anchor 10. When the spinal fixation element 18 is fixed relative to the receiver member 16, the proximal head 12, and, thus, the bone anchor 10, can move relative to the bearing 20. To reduce wear on the bearing 20, the bearing 20 may be constructed from a wear resistant material, such as, for example, fiber reinforced polymer, such as fiber reinforced PEEK, e.g. carbon fiber reinforced PEEK. Other wear resistant materials can include UHMWPE, PEEK, polycarbonate urethane, and wear resistant ceramics and metals.

Continuing to refer to FIGS. 1-3, and FIGS. 8 and 9, the insert 24 is positioned in the proximal end 26 of the receiver member 16 and has a pair of spaced apart insert arms 28A, 28B defining a U-shaped recess 30 therebetween that is sized and shaped to receive the spinal fixation element 18. Each insert arm 28A, 28B aligned with and positioned against an interior surface of a respective arm 42A, 42B of the receiver member 16. The insert 24 of the exemplary embodiment includes a distal end 72 that is general annular in shape and has a diameter greater than the distance between the outer surfaces of the proximal end 62A, 62B of the bearing 20 such that the proximal ends 62A, 62B of the bearing 20 fit within the distal end 72 of the insert 30. Each insert arm 28A, 28B extends from the annular distal end 72 of the insert 24 to a free, proximal end 74A, 74B. Each insert arm 28A, 28B may include a feature for engaging the closure mechanism 32. In the exemplary embodiment, each insert arm 28A, 28B includes an internal thread 76 on the interior surface of the insert arm 28A, 28B for engaging the closure mechanism 32. In the exemplary embodiment, the thread 76 starts at the free, proximal end 74A, 74B and extends distally along at least a portion of the length of the insert arms 28A, 28B.

Each insert arm 28A, 28B includes a ridge 78A, 78B on an outer surface of the insert arm 28A, 28B. The ridges 78A, 78B may have a size and shape corresponding to the grooves 56A, 56B provide on the interior surface of the arms 42A, 42B of the receiver member 16. Once assembled, the insert arms 28A, 28B and the insert recess 30 are aligned with the arms 42A, 42B and the recess 44 of the receiver member 16 and the ridges 78A, 78B are seated within the grooves 56A, 56B to prevent axial movement of the insert 24 with the receiver member 16.

The closure mechanism 32 in the exemplary embodiment is a set screw having an external thread that engages the internal thread 76 of the insert to capture a spinal fixation element within the recess 30 of the insert 24 and, when fully tightened, to fix the spinal fixation element 18 relative to the receiver member 16. Alternatively, the closure mechanism may be dual closure mechanism having an inner and an outer set screw, such as, for example, the Expedium Dual Innie Polyaxial Screw available from DePuy Spine, Inc. of Raynham, Mass. In addition, the closure mechanism may be a non-threaded twist in cap, such as, for example, the Monarch Typhoon Cap available from DePuy Spine, Inc. of Raynham, Mass., and described in U.S. Pat. No. 6,755,829, incorporated herein by reference.

The spinal fixation element 18 in the exemplary embodiment is a rigid spinal rod. The spinal rod may be constructed titanium, titanium alloys, stainless steel, cobalt chrome, PEEK, or other materials suitable for rigid fixation. Alternatively, the spinal fixation element 18 may be a dynamic stabilization member that allows controlled mobility between the instrumented vertebrae.

Figure 10:
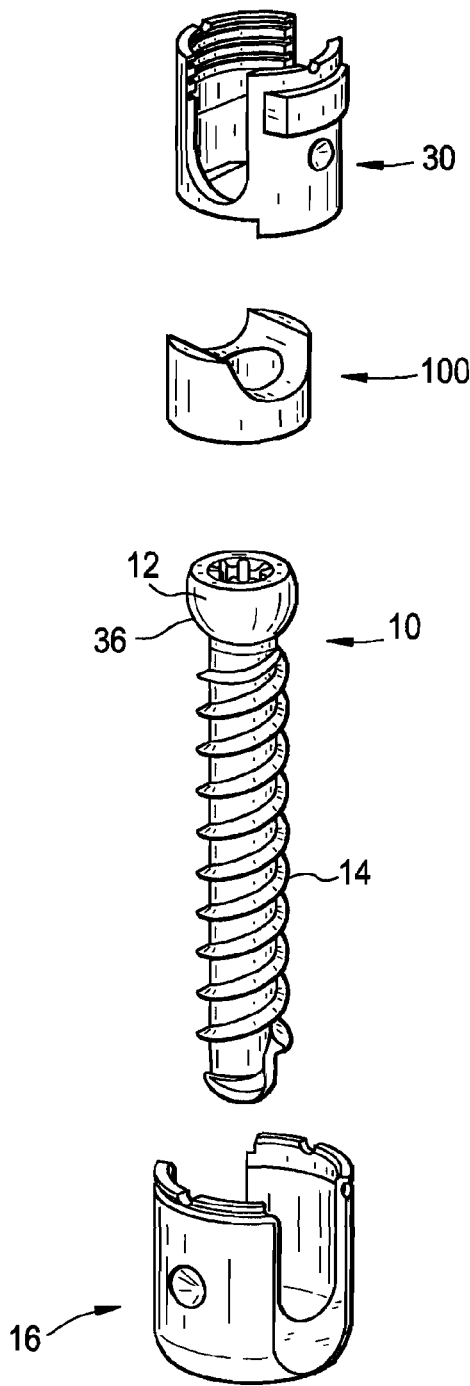
FIG. 10 is an exploded view of another exemplary embodiment of a bone anchor assembly.
Figure 11:
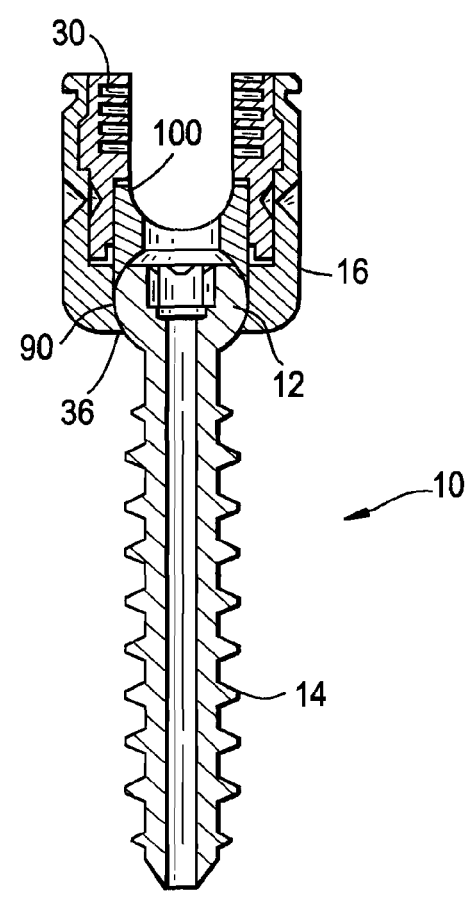
FIG. 11 is a side view in cross section of the bone anchor assembly of FIG. 10.

In alternative embodiments, the bone anchor assembly may be a rigid polyaxial screw in which the bone anchor 10 is fixed, rather than mobile, when the spinal fixation element 18 is fixed to the receiver member 16 of the bone anchor assembly, as illustrated in FIGS. 10-11. In such embodiments, the bearing 20 may be eliminated and the spinal fixation element 18 may either directly contact the proximal head 12 of the bone anchor 10 or may contact an intermediate element, e.g., a compression member 100, interposed between the spinal fixation element 18 and the proximal head 12 of the bone anchor 10 to compress the distal outer surface of the proximal head 12 into direct, fixed engagement with the distal inner surface 90 of the receiver member 16. In such embodiments, the proximal head 12 of the bone anchor 10 engages the distal inner surface 90 in a ball and socket like arrangement in which the proximal head 12, and thus the distal shaft 14, can pivot relative to the receiver member 16. The distal surface 36 of the bone anchor 10 and the distal inner surface 90 of the receiver member 16 may have any shape that facilitates this ball and socket like arrangement, including, for example, spherical (as illustrated), toroidal, conical, frustoconical, polyhedral, and any combinations of these shapes.

An exemplary method of assembling the bone anchor assembly includes inserting the distal shank 14 of the bone anchor 10 through the distal opening 50 in the distal end 22 of the receiver member 16. The bearing 20 and the proximal head 12 of the bone anchor 10 may be positioned within the distal end 22 of the receiver member 16. The bearing 20 may be positioned about the proximal head 12 of the bone anchor 10 prior to inserting the proximal head 12 into the receiver member 16 and, thus, the bearing 20 and the proximal head 12 are positioned collectively into the receiver member 16. Alternatively, the proximal head 12 and the bearing 20 may be positioned separately into the receiver member 16. If the bearing 20 is a multi-part construct, for example, a two part construct as described above, the first bearing component 60A, and the second bearing component 60B may be positioned about the proximal head 12 of the bone anchor 10. Once positioned in the receiver member 16, the distal end surface 69 of the bearing 20 may be positioned against the inner distal end surface 90 of the distal end 22 of the receiver member 16 such that at least a portion of the bearing 20 is interposed between the proximal head 20 and the inner distal end surface 90 of the distal end 22 of the receiver member 16. In addition, the distal opening 68 of the bearing 20 is aligned with the distal opening 50 of the receiver member 16 and the distal shaft 14 of the bone anchor 10 extends through the distal opening 68 of the bearing 20 and the distal opening 50 of the receiver member 16.

The insert 24 may be positioned within the receiver member 16. Each insert arm 28A, 28B may be aligned with a respective arm 42A, 42B of the receiver member 16 and the U-shaped recess 30 of the insert 24 may be aligned with the recess 44 in the proximal end 26 of the receiver member 16. The insert 24 may be secured to the receiver member 16 by positioning each of the ridges 78A, 78B within a respective one of the grooves 56A, 56B provided on the interior surface of the receiver member 16. In one exemplary embodiment, the insert 24 may be oriented such that the insert arm 28A, 28B are positioned in the space between the arms 42A, 42B of the receiver member 16 and the insert 24 may be then rotated approximately 90° to align the insert arms 28A, 28B with the receiver member arms 42A, 42B and position the ridges 78A, 78B within the grooves 56A, 56B provided on the interior surface of the receiver member 16.

The exemplary bone anchor assembly may be used with other bone anchor assemblies and a spinal fixation element to fix multiple vertebrae. In one exemplary method of use, the spinal fixation element 18 may be positioned within the recess 30 of the insert 24 and, thus, the recess 44 of the receiver member 16. A closure mechanism 32 may be connected to the receiver member 16 by connecting the closure mechanism 32 to the insert 24. For example, the closure mechanism 32 when in the form of a set screw may be rotated into engagement with the internal thread 76 provided on the arms 28A, 28B of the insert 24. As the closure mechanism 32 is tightened by advancing the closure mechanism 32 distally, the closure mechanism 32 contacts the spinal fixation element 18 and advances the spinal fixation element 18 into engagement with the U-shaped seat 66 defined by the proximal ends 62A, 62B of the bearing 20. The distal force provided on the spinal fixation element 18 by the closure mechanism 32 during tightening is transmitted through the bearing 20 to the receiver member 16, and not to the proximal head 12 of the bone anchor 10, as the bearing 20 is interposed between the proximal head 12 and the inner distal end surface 90 of the distal end 22 of the receiver member 16. During tightening, the bearing components 60A, 60B may separate slightly as the spinal fixation element 18 is moved distally into the U-shaped seat 66. The tightening of the closure mechanism 32 imparts a proximal force on the insert 24 with respect to the receiver member 16. The interaction of the ridges 78A, 78B on the insert 24 within the grooves 56A, 56B receiver member 16 prevents separation of the insert 24 from the receiver member 16 and fixes the insert 24 relative to the receiver member 16. Once the closure mechanism 32 is fully tightened, the spinal fixation element 18, the insert 24, the bearing 20, and the receiver member 16 are fixed with respect to each other and the proximal head 12 of the bone anchor 10 remains free to move with respect to the bearing 20, and thus, the receiver member 16 and the spinal fixation element 18.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

What is claimed is:

1. A bone anchor assembly comprising:
   a bone anchor having a proximal head and a distal shaft configured to engage bone,
   a receiver member for receiving a spinal fixation element to be coupled to the bone anchor, the receiver member having
      a proximal end having a pair of spaced apart arms defining a recess therebetween,
      a distal end having a distal end surface defining opening through which at least a portion of the bone anchor extends,
   a bearing positioned in the distal end of the receiver member and receiving the proximal head of the bone anchor, at least a portion of the bearing interposed between the proximal head of the bone anchor and the distal end surface of the distal end of the receiver member,
   an insert positioned in the proximal end of the receiver member, the insert having a pair of spaced apart insert arms defining a recess therebetween, the recess being sized and shaped to receive a spinal fixation element, each insert arm aligned with and positioned against an interior surface of a respective arm of the receiver member, the insert including an annular shaped distal end, the annular shaped distal end being positioned about a portion of the bearing and engaging the bearing when the spinal fixation element is fixed to the receiver member, and
   a closure mechanism positionable between and engaging the insert arms to capture a spinal fixation element within the recess of the insert and fix the spinal fixation element with respect to the receiver member.

2. The bone anchor assembly of claim 1, wherein the proximal head of the bone anchor is in the shape of a truncated sphere having a planar proximal surface and an approximately spherically shaped distal surface.

3. The bone anchor assembly of claim 2, wherein the bearing has a proximal end defining a U-shaped seat for receiving the spinal fixation element.

4. The bone anchor assembly of claim 3, wherein the bearing has a distal end having a distal opening that aligns with the distal opening in the distal end of the receiver member, at least a portion of the bone anchor extending through the distal opening in the bearing and the distal opening in distal end of the receiver member.

5. The bone anchor assembly of claim 4, wherein the distal end of the bearing surrounds the proximal head of the bone anchor.

6. The bone anchor assembly of claim 4, wherein the distal end of the bearing has an internal surface having an approximately spherical shape.

7. The bone anchor assembly of claim 6, wherein the internal surface of the distal end of the bearing has a curvature that approximates a curvature of the proximal head of the bone anchor.

8. The bone anchor assembly of claim 4, wherein the bearing is a multi-piece construct.

9. The bone anchor assembly of claim 1, wherein the bone anchor is adjustable relative to the bearing and the receiver member after the rod is fixed relative to the receiver member.

10. The bone anchor assembly of claim 1, wherein the bearing is constructed from fiber reinforced PEEK.

11. The bone anchor assembly of claim 1, wherein each insert arm includes an internal thread on an interior surface of the arm and the closure mechanism is a set screw.

12. The bone anchor assembly of claim 1, wherein each insert arm includes a ridge on an outer surface of the arm, the ridge being sized and shaped to fit within a groove provided on the interior surface of the arm of the receiver member.

13. A method of assembling a bone anchor assembly, the method comprising:
   inserting a distal shank of a bone anchor through a distal opening in a distal end of a receiver member, the receiver member having a proximal end having a pair of spaced apart arms defining a recess therebetween,
   inserting a bearing and a proximal head of the bone anchor within the distal end of the receiver member,
   positioning the bearing about the proximal head of a bone anchor,
   positioning the bearing against a distal end surface of the distal end of the receiver member, at least a portion of the bearing being interposed between the proximal head and the distal end surface of the distal end of the receiver member,
   positioning an insert having a pair of opposed arms forming a U-shaped recess within the receiver member with each arm of the insert positioned in a space between the spaced-apart arms of the receiver member, the U-shaped recess being sized and shaped to receive a spinal fixation element,
   rotating the insert about its central longitudinal axis to align each insert arm with an interior surface of a respective arm of the receiver member and the U-shaped recess of the insert with the recess in the proximal end of the receiver member, and
   securing the insert to the receiver member.

14. The method of claim 13, wherein securing the insert to the receiver member includes positioning a ridge on an outer surface of each insert arm within a groove provided on the interior surface of the arm of the receiver member.

15. The method of claim 14, wherein the distal end of the bearing has an internal surface having an approximately spherical shape.

16. The method of claim 13, further comprising positioning an annular shaped distal end of the insert about a portion of the bearing.

17. The method of claim 16, wherein annular shaped distal end of the insert is positioned about a U-shaped proximal end of the bearing, the U-shaped proximal end of the bearing forming a seat for receiving the spinal fixation element.

18. The method of claim 13, further comprising aligning a distal opening in the distal end of the bearing with the distal opening in the distal end of the receiver member and positioning at least a portion of the bone anchor through the distal opening in the bearing and the distal opening in distal end of the receiver member.

19. The method of claim 13, wherein positioning a bearing about a proximal head of a bone anchor includes positioning the distal end of the bearing about the proximal head of the bone anchor.

20. The method claim 13, wherein the bearing is a two part construct and wherein positioning the bearing about the proximal head of a bone anchor includes positioning a first component of the bearing about the proximal head of the bone anchor and positioning a second component about the proximal head of the bone anchor.

\* \* \* \* \*